(12) United States Patent
Vannuffelen et al.

(10) Patent No.: US 7,933,018 B2
(45) Date of Patent: Apr. 26, 2011

(54) SPECTRAL IMAGING FOR DOWNHOLE FLUID CHARACTERIZATION

(75) Inventors: Stephane Vannuffelen, Tokyo (JP); Ahmed Hammami, Alberta (CA); Toru Terabayashi, Sagamihara (JP); Tsutomu Yamate, Yokohama (JP); Terry Sopkow, Alberta (CA); John Ratulowski, Missouri City, TX (US); John A. Kerr, Sugar Land, TX (US); Francois Auzerais, Houston, TX (US); Robert J. Schroeder, Newtown, CT (US); Jeffrey A. Tarvin, Brookfield, CT (US); Andrew L. Kurkjian, Sugar Land, TX (US); Laurent Prouvost, Ambares et Lagrave (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 235 days.

(21) Appl. No.: 11/204,134

(22) Filed: Aug. 15, 2005

(65) Prior Publication Data
US 2007/0035736 A1   Feb. 15, 2007

(51) Int. Cl.
*G01N 21/00* (2006.01)
(52) U.S. Cl. .................. 356/432; 356/436; 356/441
(58) Field of Classification Search .............. 73/152.01, 73/152.55; 356/241.1, 432–434, 436, 626–627
See application file for complete search history.

(56) References Cited

U.S. PATENT DOCUMENTS

| | | | | |
|---|---|---|---|---|
| 4,994,671 A | * | 2/1991 | Safinya et al. | 250/255 |
| 5,162,647 A | * | 11/1992 | Field, Jr. | 250/214 VT |
| 5,790,185 A | | 8/1998 | Auzerais et al. | |
| 2004/0211894 A1 | * | 10/2004 | Hother et al. | 250/269.1 |
| 2005/0134845 A1 | * | 6/2005 | Bordelon | 356/336 |

FOREIGN PATENT DOCUMENTS

| | | |
|---|---|---|
| EP | 0747569 A2 | 12/1996 |
| GB | 2399971 A | 9/2004 |
| WO | WO 96/41066 A1 | 12/1996 |
| WO | WO 99/00575 A2 | 1/1999 |
| WO | WO 99/60249 A1 | 11/1999 |
| WO | WO 01/40771 A2 | 6/2001 |
| WO | WO 02/06631 A1 | 1/2002 |
| WO | WO 2004/083833 A1 | 9/2004 |

OTHER PUBLICATIONS

Martin, James S., "The Use of a Combine Polarizing Light/Epi-fluorescence Microscope for Examination and Analysis of Painted and Coated Objects and Samples." Jun. 1996. Postprints of the Wooden Artifacts Group, pp. 19-21.*

(Continued)

*Primary Examiner* — Tarifur Chowdhury
*Assistant Examiner* — Tara S Pajoohi
(74) *Attorney, Agent, or Firm* — Daryl Wright; Jody DeStefanis; Jeff Griffin

(57) ABSTRACT

The present invention contemplates implementation of transitory downhole video imaging and/or spectral imaging for the characterization of formation fluid samples in situ, as well as during flow through production tubing, including subsea flow lines, for permanent and/or long term installations. The present invention contemplates various methods and apparatus that facilitate one-time or ongoing downhole fluid characterization by video analysis in real time. The methods and systems may be particularly well suited to permanent and periodic intervention-based operations.

15 Claims, 17 Drawing Sheets

(7 of 17 Drawing Sheet(s) Filed in Color)

OTHER PUBLICATIONS

Hammami, et al., "Paraffin Deposition From Crude Oils: Comparison of Laboratory Results to Field Data", SPE Journal, 1999, vol. 4, pp. 9-18.

Hammami, et al., "Asphaltene Precipitation From Live Oils: An Experimental Investigations of the Onset Conditions and Reversibility", Energy & Fuels, 2000, vol. 14, pp. 14-18.

Karan, et al., "Evaluation of Asphaltene Instability and a Chemical Control During Production of Live Oils", Pel. Sci & Tech. 2003. vol. 21 No. 3 & 4, 2003, pp. 629-645.

Levenson, et al., "Spectral Imaging and Microscopy", American Laboratory, 2000, pp. 1-8.

Gat, "Imaging Spectroscopy Using Tunable Filters: A Review", Proc SPIE, p. 50-64, vol. 4056, Wavelel applications VI.

Herman, et al., "Compact Hyperspectral Imager for Low Light Applications".

http://www.dhvi.com/.

Staenz, et al., "Evaluation of CASI and SFSI Hyperspectral Data for Enviromental and Geological Applications—Two Case Studies", pp. 1-12, at http://www.borstad.com/papers/eval_casi_sfsi.html.

Y. Inouo, J. Panuelas, "An AOTF-based hyperspectral imaging system for hold use in ecophysiological and agricultural applications", Int. J. Remote Sensing, 2001, vol. 22, No. 18, pp. 3883-3888.

* cited by examiner

PRIOR ART

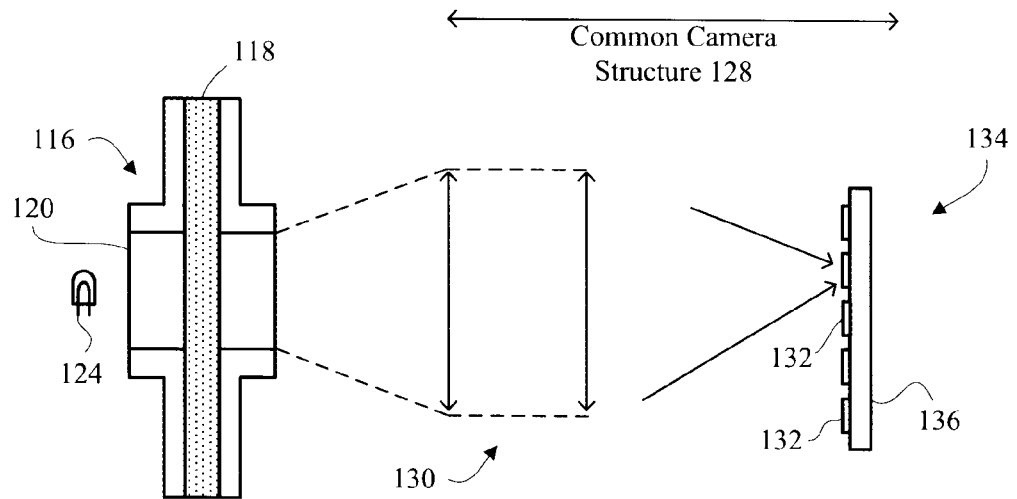

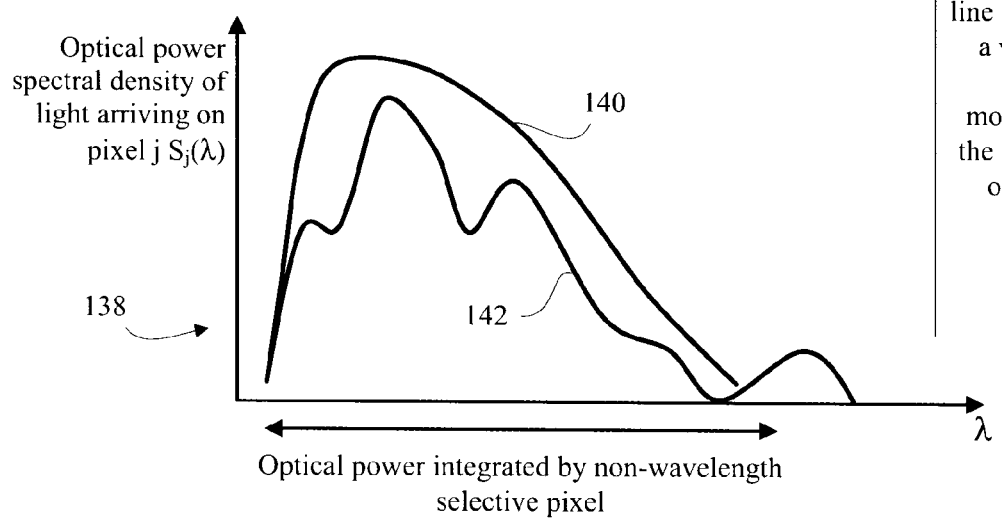

Optical power spectral density of light arriving on pixel j $S_j(\lambda)$

Sample in flow line 118 generates a wavelength selective modification of the light arriving on the pixel Optical power integrated by non-wavelength selective pixel Electrical signal generated at the output of each pixel is proportional to:

$$\int S_j(\lambda)G_j(\lambda)d\lambda$$

Spectral information is lost

FIG. 6

SPECTRAL IMAGING FOR DOWNHOLE FLUID CHARACTERIZATION

FIELD OF THE INVENTION

The present invention relates generally to methods and systems for investigating subterranean formation fluids. More particularly, this invention is directed to methods and systems for spectral imaging to characterize downhole fluids.

BACKGROUND OF THE INVENTION

Fluid characterization is very important to the assessment of economic viability for a hydrocarbon-bearing reservoir formation. Some wireline tools such as Schlumberger's MDT (Modular Dynamic Tester) are used to sample formation fluids, store it in a set of bottles, and retrieve it to surface while keeping the fluid pressurized. Such samples. are known as live fluids. These live fluids are then sent to an appropriate laboratory to be characterized. Characterization of the fluids may include composition analysis, fluid properties and phase behavior.

Understanding reservoir fluid phase behavior is key to proper planning and development of the respective fields and design of the production system. Understanding reservoir fluid phase behavior involves conducting a number of very important measurements on the fluid at realistic reservoir and production conditions. In most cases, changes in temperature (T) and pressure (P) of the formation fluid lead to phase changes, including phase separation (e.g., liquid-vapor, liquid-solid, liquid-liquid, vapor-liquid etc.), and phase recombination. For example, while most hydrocarbons exist as a single phase at initial reservoir conditions (i.e., composition, pressure, and temperature), they often undergo reversible (and possibly some irreversible) multi-phase changes due to pressure, composition and/or temperature reduction during production and flow to the surface facilities. FIG. 1 illustrates a typical phase diagram measured for an under-saturated live oil prone to precipitate asphaltene, wax, and hydrate during production.

Liquid-Solid-Vapor phase boundaries are typically measured at a laboratory using state-of-the-art-technologies, such as Schlumberger's pressure-volume-temperature (PVT) unit coupled to Schlumberger's laser-based Solids Detection System (SDS) and Schlumberger's high-pressure microscope (HPM). Detailed descriptions of these state-of-the art technologies and their applications for the study of phase behavior and flow assurance of petroleum fluids have been published and are known to those of skill in the art.

The HPM is currently used in a laboratory environment to characterize formation fluids. FIGS. 2a-2b illustrate examples of an HPM study with snapshots of a fluid before and after a phase transition point:

FIG. 2a shows an example of asphaltene onset pressure measurement at reservoir temperature ($T_{res}$).

FIG. 2b shows the formation of liquid-liquid split above the saturation pressure of a reservoir fluid at $T_{res}$.

The HPM (typically equipped with a cross polarizer) makes it possible to quantify particle or bubble size. Moreover, it is possible to make a clear distinction between wax, asphaltene, oil phase, water droplets, and hydrate crystals when the multiple components are coexisting as evidenced in FIG. 2-c and 2-d.

However, the current trend in the wireline industry is to perform more and more analysis of the formation fluid properties directly downhole to avoid the difficulties associated with sample preservation when lifted uphole and delays associated with sample transportation and analysis in a remote laboratory. Tools like Schlumberger's MDT can, for example, be retrofitted with a spectrometer module such as a Live Fluid Analyser or Gas Condensate Analyser in order to provide basic information on the fluid composition (Gas-to-oil ratio (GOR), water content, basic crackdown of hydrocarbon fractions ($C_1$, $C_2$-$C_5$, $C_6$+)). These measurements are performed by infrared (IR) absorption spectroscopy. FIG. 3 presents a typical absorption spectrum of a typical oil and of other species present in the oil, such as water. Characteristic absorption peaks can therefore be measured, especially in the near IR (NIR) range.

Nevertheless, current measurements of certain downhole characteristics such as phase behavior are not available outside of a laboratory. Video image fluid characterization is currently only available in laboratory environments as described above, yet it is desirable to analyze formations fluids in situ.

There has been some use of video imaging downhole in wireline tools, but current technology is limited to applications related to production logging. Current downhole imaging is dedicated to borehole wall imaging and has low spatial resolution. DHV International, for example, provides downhole video services to the oil and gas industry for diagnosis of borehole problems such as fishing out lost tools, mechanical inspection, and fluid entry surveys. There are currently no methods or systems for fully characterizing formation fluids downhole.

In addition to characterizing formation fluids at well assessment stages, the understanding of phase behavior is also extremely important during the production phase of well operations. As mentioned above, during production, the formation fluids cool down and depressurize as they travel from the reservoir to the surface. The fluids can undergo several phase changes that are currently not very well understood. These phase changes can lead to serious problems, especially if a solid phase precipitate (such as wax or asphaltene) forms. In certain conditions, these solids can stick to wall casing, forming a solid deposit and eventually decrease well productivity by increasing the resistance to flow (reduced hydraulic diameter of the tubing) or build-up a plug. Similar problems can especially take place in a subsea environment along the pipelines used to carry oil from a production well to onshore environments.

Accordingly, the introduction of phase behavior monitoring downhole during production would be a significant breakthrough in order to optimize production conditions and reduce/control the risk of solid phase precipitation and, in turn, deposition.

The present invention is direct to overcoming, or at least reducing the effects of, one or more of the problems presented above.

SUMMARY OF THE INVENTION

The present invention meets the above-described needs and others. Specifically, the present invention provides a method of monitoring subterranean formation fluids, especially applicable but not limited to hydrocarbons. The method includes characterizing a formation fluid sample downhole with a video imaging system, where the video imaging system performs pixel imaging and additional imaging. The additional imaging may comprise spectral imaging using a spectrally broadband light source in combination with a spectral imaging video camera downhole, or using a tunable or multi-wavelength light source in combination with any camera.

The characterizing may further include characterizing a fixed sample in the video imaging system. Preparation for characterizing may include pumping a formation fluid sample, into a sample cell downhole, isolating the fluid sample, and controlling pressure and volume of the isolated fluid sample.

According to some aspects of the invention, characterization comprises two or three-dimensional imaging and analysis.

According to some embodiments, the characterizing further comprises flowing the fluid sample through the video imaging system. Accordingly, the characterization may comprise one-dimensional, in-line imaging and analysis. The one-dimensional imaging may comprise successively acquiring one-dimensional flow line images and reconstituting two or more of the one-dimensional flow line images into a two-dimensional image.

According to some aspects of the invention, the method may include actively cooling the video imaging system downhole.

Some aspects of the invention may include relaying video imaging data from the video imaging system uphole via a telemetry bus or temporarily storing the captured images in suitable and retrievable downhole memory chips.

Another aspect of the present invention provides a downhole fluid characterization apparatus. The apparatus comprises a downhole lab module, which includes a sample flow line, a sample cell in fluid communication with the sample flow line, the sample cell comprising at least one transparent window, a light source adjacent to the sample cell, and a camera for imaging fluids downhole. The apparatus may include an active cooling system for cooling the camera downhole. At least one transparent window may comprise sapphire. The light source and camera may comprise a transmission or backscattered imaging configuration. The camera may be a spectral camera. The spectral camera may include an imaging optic and an image sensor. According to some embodiments, the light source comprises a tunable or multi-wavelength light source, and the camera comprises a broadband camera. The camera may be a one-dimensional camera.

According to some aspects of the invention, the downhole lab module further comprises a pressure-volume control unit. The apparatus may also include a downhole video module for sample quality assurance. The downhole video module may include a second sample cell in fluid communication with the sample flow line, the second sample cell comprising at least one transparent window, a second light source adjacent to the second sample cell, and a second camera for imaging fluids downhole.

According to some aspects of the invention, the apparatus comprises a telemetry bus operatively connected to the camera.

According to some aspects, the downhole lab module may comprise a portion of a wireline tool. The downhole lab module may also be permanently installed downhole, and in fluid communication with, a production line.

Another aspect of the invention provides a method of characterizing formation fluids downhole, comprising inserting a sample flow line, a light source, and a camera into a wellbore, positioning the sample flow line, light source, and camera adjacent to a formation of interest, passing a formation fluid of interest into the flow line, and imaging the formation fluid of interest downhole with the camera. The method may further comprise telemetering imaging data from the camera uphole to an operator in real time. The method may include actively cooling at least the camera downhole. The method may include illuminating the formation fluid of interest sequentially at different spectral regions with a wavelength selective light source, synchronizing image acquisition with light spectrum sequence, and producing an image for each spectral region. The imaging may further comprise spatial imaging showing a location of components of the formation fluid of interest, and spectral imaging showing optical absorption.

Another aspect of the invention provides a method of wellbore production. The method comprises flowing formation fluids from a formation through a production line, passing a portion of the formation fluids through a first permanent downhole lab module in a first location, imaging the portion of formation fluids with a first downhole camera of the first permanent downhole lab module, and transmitting imaging data uphole. The method may further include analyzing the imaging data uphole and adjusting production parameters based on the imaging data. The method may include passing a portion of the formation fluids through a second permanent downhole lab module in a second location (which may be downstream from the first location), imaging the portion of the formation fluids with a second downhole camera of the second permanent downhole lab module, and transmitting imaging data uphole from the second downhole camera. The method may further include adjusting chemical injection parameters based on the imaging data from the first and second downhole cameras. Additional similar or identical set ups may be installed along the production flow lines down stream of the first location.

Another aspect of the invention provides a method of characterizing formation fluids downhole. The method comprises flowing formation fluids from a formation into a downhole pressure-volume control unit, adjusting a pressure of the formation fluids contained by the downhole pressure-volume control unit, imaging the formation fluids contained by the downhole pressure-volume control unit with a first downhole camera, and transmitting imaging data uphole. The adjusting of the pressure may comprise reducing the pressure to induce phase changes downhole at a constant depth. The imaging may comprise video recording the formation fluids downhole as pressure is reduced and detecting phase changes.

Additional advantages and novel features of the invention will be set forth in the description which follows or may be learned by those skilled in the art through reading these materials or practicing the invention. The advantages of the invention may be achieved through the means recited in the attached claims.

The accompanying drawings illustrate preferred embodiments of the present invention and are a part of the specification. Together with the following description, the drawings demonstrate and explain the principles of the present invention. The patent or application file contains at least one drawing executed in color. Copies of this patent or patent application publication with color drawings will be provided by the U.S. Patent and Trademark Office upon request and payment of the necessary fee.

BRIEF DESCRIPTION OF THE DRAWINGS

FIG. 6 illustrates a downhole fluid characterization technique using a black and white camera for imaging according to one aspect of the present invention.

Throughout the drawings identical reference numbers designate similar, but not necessarily identical elements.

DETAILED DESCRIPTION OF THE PREFERRED EMBODIMENTS

Figure 1:
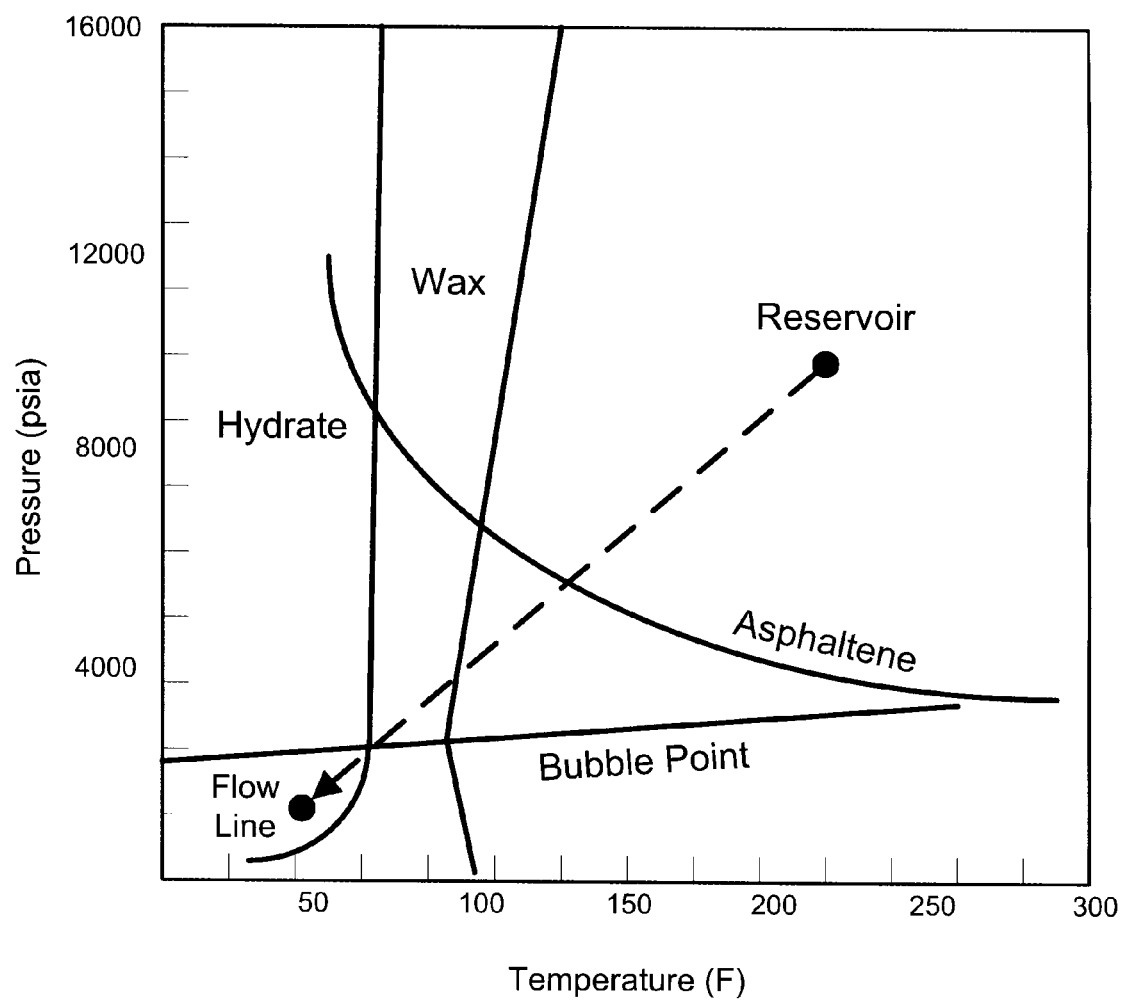
FIG. 1 is an example of a phase diagram measured for a live unstable oil according to one aspect of the present invention.
Figure 2A:
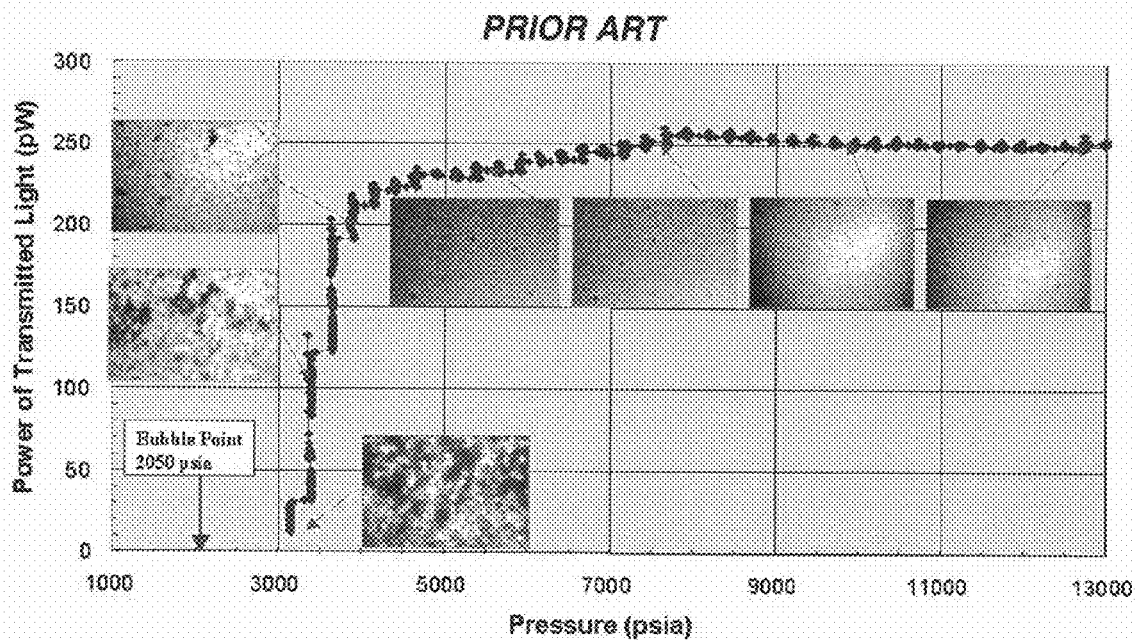
FIG. 2a is an example of phase behavior analysis related to asphaltene onset available using video imaging.
Figure 2B:
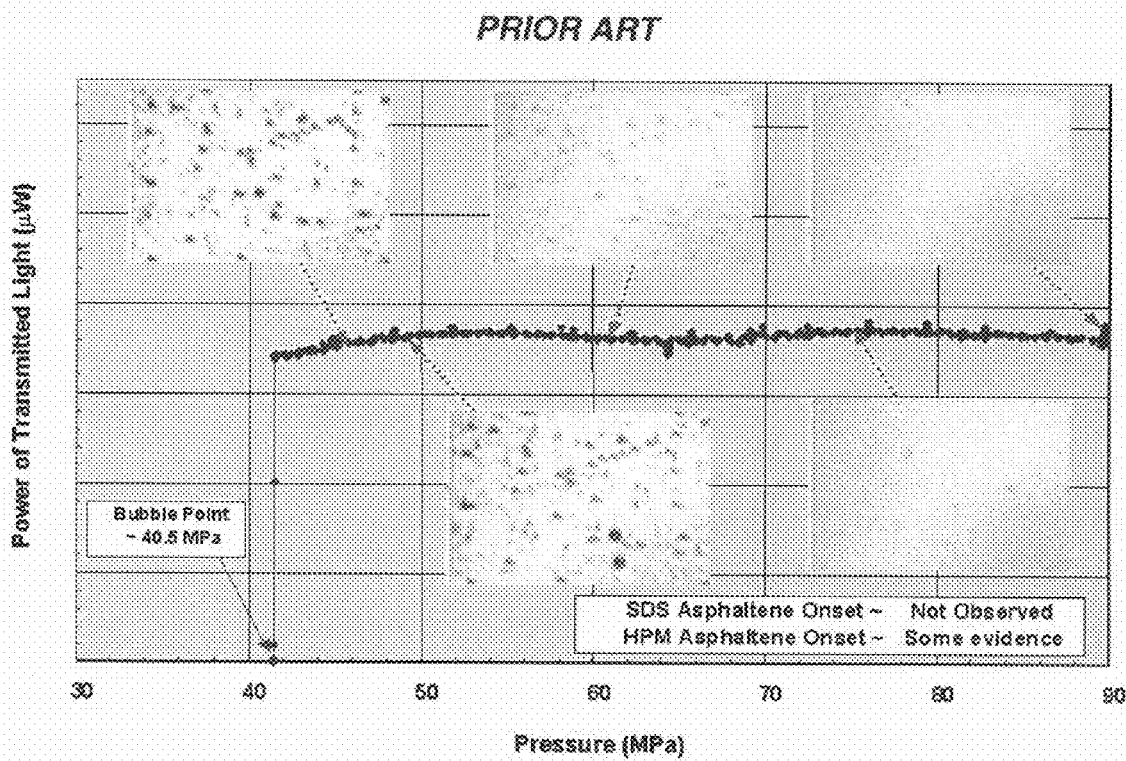
FIG. 2b is an example of phase behavior analysis related to liquid-liquid split above the saturation pressure of a reservoir fluid at Tres available using video imaging.
Figure 2C:
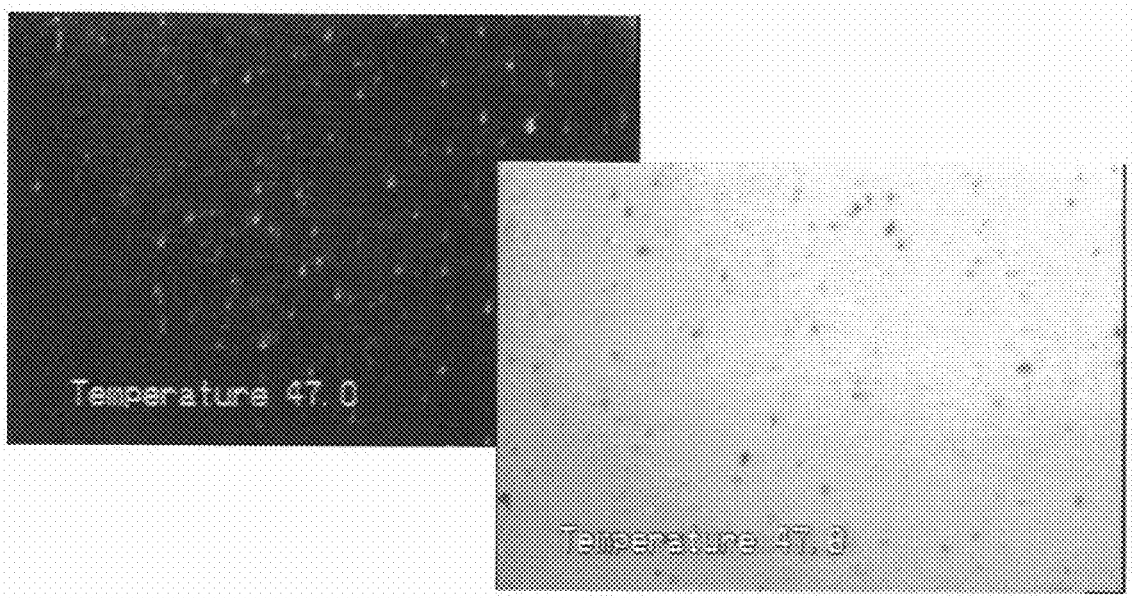
FIG. 2c illustrates evidence of wax-asphaltene co-precipitation during isobaric cooling of reservoir fluid available using video imaging.
Figure 2D:
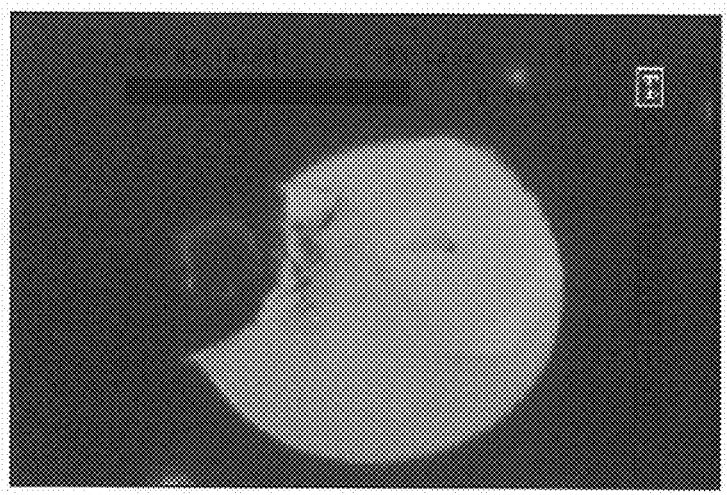
FIG. 2d illustrates evidence of hydrate crystal at a water droplet-heavy oil interface available using video imaging.

Illustrative embodiments and aspects of the invention are described below. It will of course be appreciated that in the development of any such actual embodiment, numerous implementation-specific decisions must be made to achieve the developers' specific goals, such as compliance with system-related and business-related constraints, that will vary from one implementation to another. Moreover, it will be appreciated that such a development effort might be complex and time-consuming, but would nevertheless be a routine undertaking for those of ordinary skill in the art having the benefit of this disclosure.

The present invention contemplates implementation of downhole video imaging and spectral video imaging for the characterization of formation fluid samples, as well as during flow through production tubing, including subsea flow lines. The present invention contemplates various methods and apparatus that facilitate ongoing downhole fluid characterization by video analysis, preferred embodiments of which are described below. The methods and systems may be particularly well suited to wireline sampling operations and wireline or slick-line conveyed production logging measurements, for which a profiling of the phase behavior of the produced fluids along the course of the wells (as pressure and temperature vary) would be particularly advantageous for optimizing well hydraulics. However, the methods and systems presented herein are not so limited. For example, the methods and systems may be applied to permanent and semi-permanent production monitoring, or other applications such as logging while drilling (LWD) and measurement while drilling (MWD). In a broader sense, the techniques described herein can be applied to fluid characterization measurements relating to any subterranean hydrocarbon reservoir and fluid production system.

As used throughout the specification and claims, the term "fluid" means a continuous, amorphous substance whose molecules move freely past one another and that has the tendency to assume the shape of its container, including both liquids, gases, emulsions (water-in-oil and oil-in-water, two or more liquid phases), and multiphase systems (liquids+gas+solids). "Transparent" means capable of transmitting light so that objects or images can be seen as if or nearly as if there were no intervening material, but not necessarily clear. The words "including" and "having," as used in the specification, including the claims, have the same meaning as the word "comprising."

The methods and systems presented herein for characterizing formation fluids downhole include a description of at least two general optical layouts. The at least two general optical layouts comprise the use of a spectrally broadband source in combination with a spectral imager such as a video camera, and the use of a tunable or multi-wavelength light source in combination with any type of camera. The principles of the present invention may include one-dimensional (1D) (in line), two-dimensional (2D), and three-dimensional (3D) imaging.

As mentioned above in the background, there is an interest in imaging techniques for characterization of downhole fluids under laboratory conditions. The laboratory imaging techniques are based on measurements in the visible light range, possibly with polarization, with a single pixel, black and white or color mode. There is also interest in visible IR-spectroscopy for the characterization of downhole fluids. Fluid absorption properties are highly related to chemical composition at light wavelengths ranging between the visible range and approximately 10 μm. According to principles of the present invention, fluid characterization may be accomplished downhole using both visible light in the black and white mode and optical spectroscopy to perform spectral imaging.

Figure 5A:
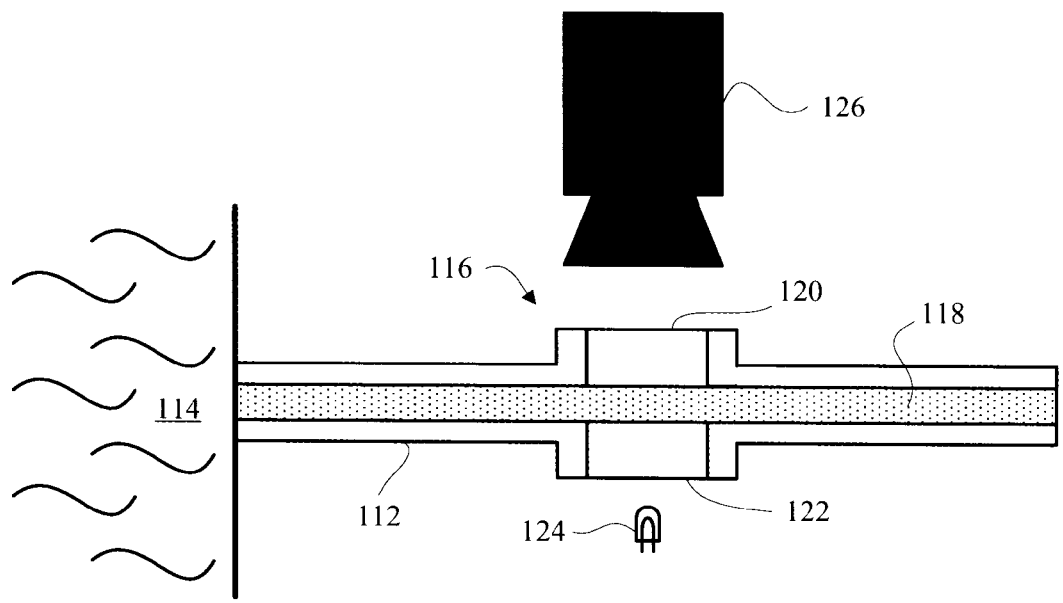
FIG. 5a illustrates a schematic of a downhole fluid sample characterization system configuration according to one aspect of the present invention.
Figure 5B:
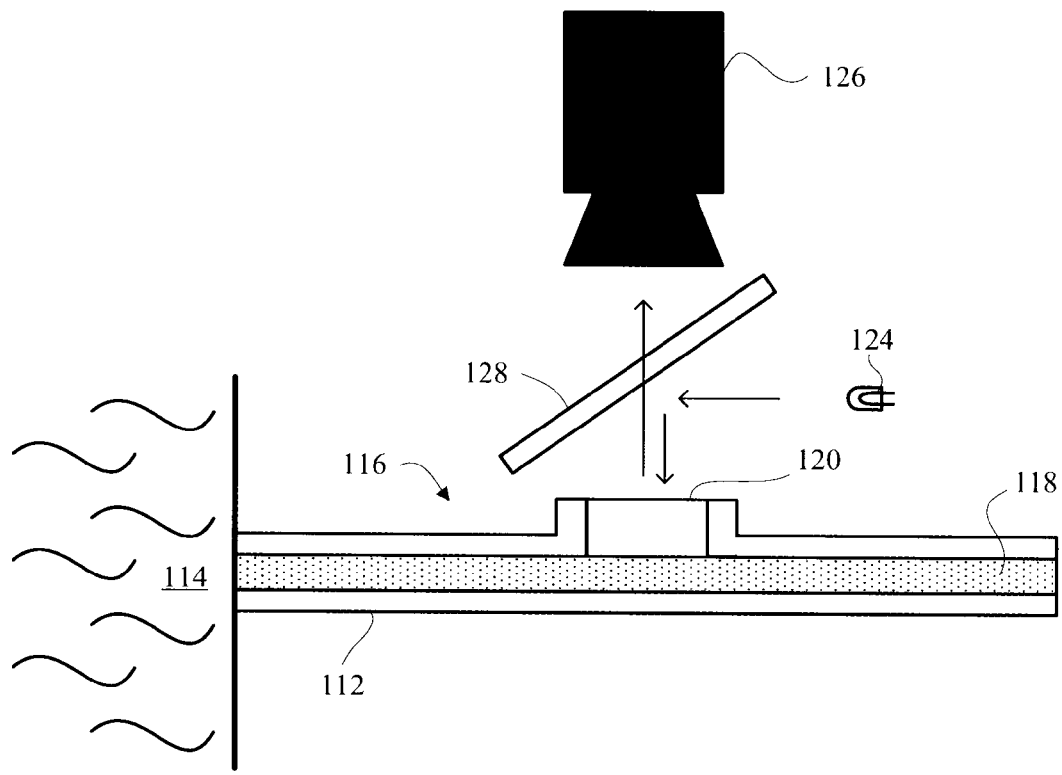
FIG. 5b illustrates a schematic of a downhole fluid sample characterization system for back-scattered imaging according to one aspect of the present invention.
Figure 5C:
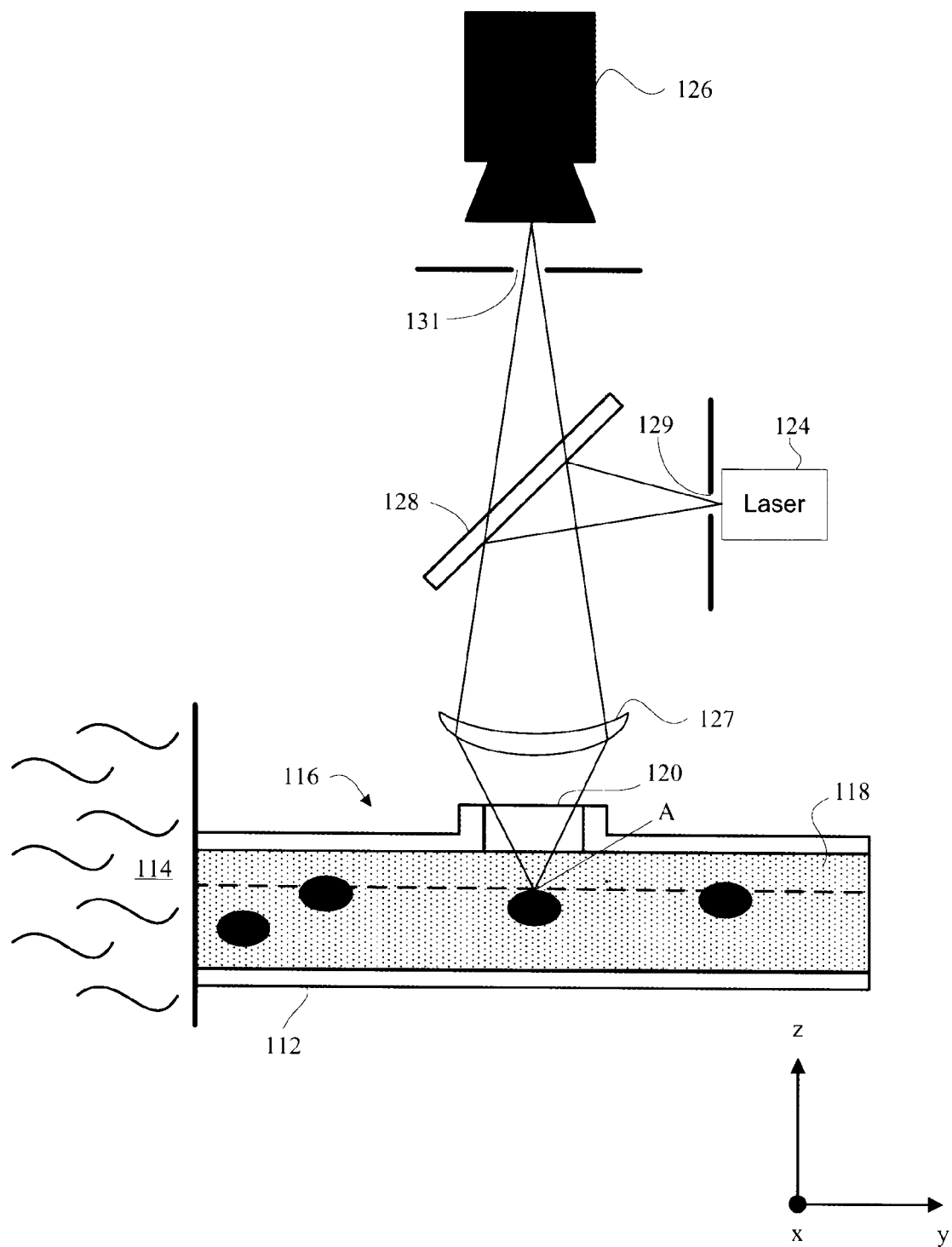
FIG. 5c illustrates a schematic of a downhole fluid sample characterization system for generating a 3D image of the flow line according to one aspect of the present invention.

Turning now to the figures, and in particular FIGS. 5a-5c, three configurations for downhole imaging according to principles of the present invention are shown. The embodiments of FIGS. 5a-5c include a fluid sampling apparatus 112 used to convey a sample fluid from a borehole 114 or formation to a sample cell 116 through a flow line 118. Additional details of the sampling apparatus 112 are discussed below.

The sample cell 116 is fluidly connected to the flow line 118. The sample cell 116 comprises one or more windows, for example first and second windows 120, 122 shown in FIG. 5a. The first and second windows 120, 122 comprise a material that is transparent to light and may be adjustable toward and way from the flow line 118 to control sample thickness as necessary. The first and second windows 120, 122 may be made, for example, of sapphire.

A light source 124 and a camera 126 are arranged adjacent to one of the first or second windows 120, 122. The light source 124 and camera 126 facilitate imaging of the fluid located inside the sample cell 116. The light source illuminates the sample in the sample cell 116. Many possible configurations of the light source 124 and camera 126 are contemplated by the present invention. Three possible configurations are shown in FIGS. 5a-5c. Each of the configurations shown in FIGS. 5a-5c includes the light source 124 generally located in front of the camera.

According to the transmission imaging configuration of FIG. 5a, the light source 124 and the camera 126 are arranged on opposite sides of the sample chamber 116. The camera 126 may therefore be disposed adjacent to the first window 120, and the light source 124 may be disposed adjacent to the second window 122. Electromagnetic radiation may therefore pass from the light source 124 through the second window 122, illuminate sample fluid, and pass through the first window 120 where it is detected by the camera 126.

In a backscatter imaging configuration as shown in FIG. 5b, the light source 124 and the camera 126 may both be arranged on the same side of the sample chamber 116. The sample chamber 116 may thus include only the first window 120. A beam splitter 128, which is shown as a tilted plate between the sample chamber 116 and the camera 126, is used to direct light to the sample chamber 116 while also allowing backscattered light to return to the camera 126. Accordingly, direct electromagnetic radiation from the light source 124 is directed to the first window 120 by the beam splitter 128, and this radiation may be reflected from the sample contained in the sample chamber and be detected by the camera 126.

In another configuration shown in FIG. 5c, 3D flow line images may be generated using a single pixel spectral imager such as camera 126. According to the configuration of FIG. 5c, confocal microscopy is applied to flow line imaging to generate 3D images. Illuminating light comes from the light source 124, which, according to FIG. 5c, is a laser that is focused on a point A located in the flow line 118. Due to the fluid properties and the interaction of the fluids with impinging light, some light entering the flow line 118 is emitted back to a confocal lens 127 (which may be part of a confocal microscope). Reflected light may be caused by refraction phenomenon due to optic index contrast in the flow line 118. Reflected light may also be due to light reemitted by the fluid in the flow line 118 itself because of fluorescence. The light emitted or reemitted from the sample fluid in the flow line 118 is collected by the confocal lens 127 and sent to the camera 126. First and second pin holes 129, 131 adjacent to the light source 124 and the camera 126, respectively, make it possible to select only the light emitted by the focusing point A. Light from below and above the focusing point A does not reach the camera 126.

The confocal lens 127 may be scanned in the (x, y) plane in order to reconstitute a 2D image of the plane parallel to (x, y) and passing through point A. By moving the confocal lens 127 assembly in the z-direction, a 3D optical image of the flow line 118 is generated. Oil, gas, and water have significant refractive index contrasts, and oil has fluorescence properties whereas water and gas do not. Therefore, confocal imaging may facilitate better understanding of phase behavior in downhole conditions, particularly for fluid interface studies and emulsion phenomenon.

In addition to or alternative to the use of a confocal microscope or confocal lens, a high pressure microscope may be implemented downhole. A cross polarizer may be arranged in front of the microscope according to some embodiments. The use of a cross polarizer may enable wax detection.

The transmission, backscatter, and 3D configurations may each be used according to the present invention. Nevertheless, the following discussion is directed primarily to the transmission configuration of FIG. 5a. However, the principles described with reference to the transmission configuration of FIG. 5a are also applicable to the other configurations as well.

The camera 126 (FIG. 5a) forms an image of the sample cell 116 in the presence of a fluid. FIG. 6 provides a more detailed overview of a camera system 128 associated with the camera 126 (FIG. 5a), which comprises an imaging optic 130 and a 1D, 2D, or 3D image sensor 132 located in an image plane 134. The imaging optic 130 is used to collect light from the sample cell 116 and re-image it on the image sensor 132. The camera 126 (FIG. 5a) may be an electronic imaging camera which uses an image sensor to convert an optical signal to electrical data. The electrical data is then processed to create an image. The output may be an image divided into elementary pixels 136, and the combination of each pixel forms the image.

Figure 4:
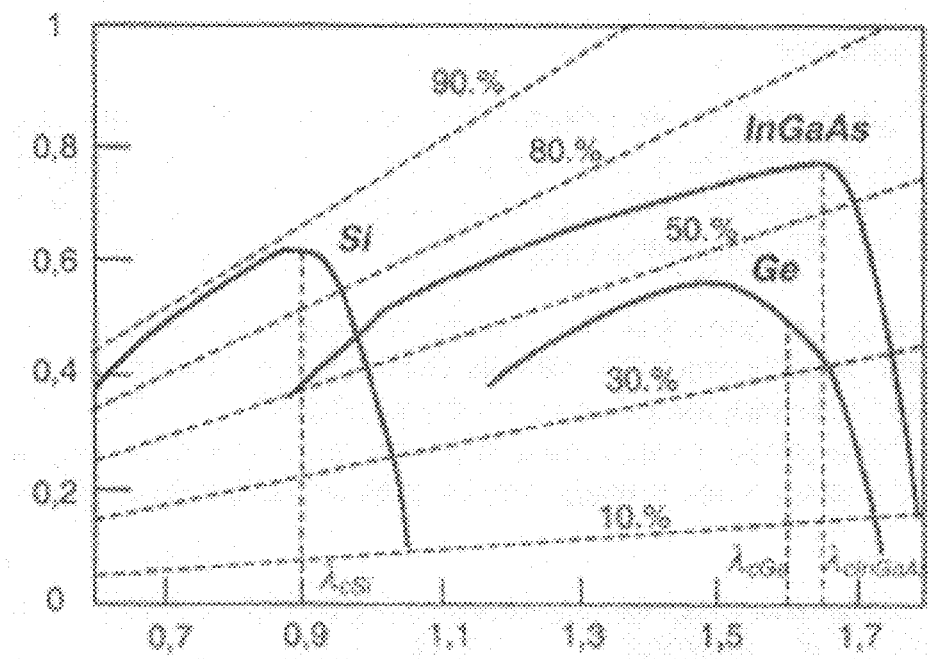
FIG. 4 illustrates a spectral response to a common image sensor currently available.

Imaging sensors (such as the imaging sensor 132 of FIG. 6) in the visible or NIR range are most commonly based on photodiodes or similar devices capable of converting light into an electrical signal. FIG. 4 displays typical wavelength sensitivity for common image sensors currently available in the desired spectral range shown. The imaging sensor 132 (FIG. 6) may therefore be considered a "broadband" sensor having poor wavelength selectivity.

Referring again to FIG. 6, the presence of a sample fluid in the sample cell 116 results in a change in the optic power spectral density arriving on the pixels 136. FIG. 6 includes a chart 138 illustrating optical power spectral density of light arriving at the pixel 136 as a function of wavelength. A first curve 140 represents light arriving at the pixel 136 without a sample fluid in the flow line 118 (FIG. 5a). A second curve 142 represents light arriving at the pixel 136 with a fluid sample in the flow line 118. A sample in the flow line 118 generates a wavelength selective modification to the light arriving at the pixel 136. An electrical signal is generated at the output of each pixel proportional to:

$$\int S_j(\lambda) G_j(\lambda) d\lambda$$

However, spectral information is lost.

Therefore, if used without an optical filtering section, the image sensors 132 produce a so-called "Black and White" (B/W) image without spectral information of the light impinging each pixel 136. This type of imaging technique may be used according to some aspects of the present invention downhole, instead of in a laboratory as described above. The B/W image allows a user to characterize the fluid without spectral information.

Figure 3:
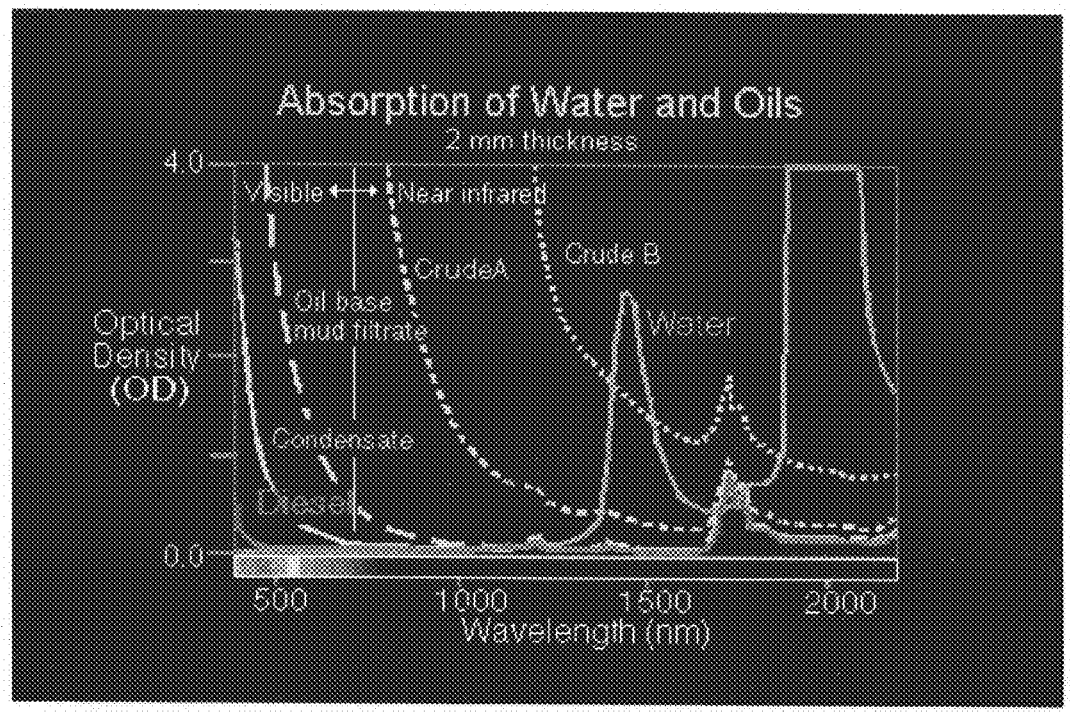
FIG. 3 is a typical absorption spectrum of oil and water in the visible/NIR range.

However, the spectral characterization of light can be used to enhance understanding of sample properties. For example, as shown in FIG. 3, absorption phenomena are indicative of sample chemistry and can lead to selective discrimination or characterization of water and oil. Therefore, in addition to imaging, according to some aspects of the present invention, analysis of wavelength dependent optical properties of a sample may be used to further characterize the sample.

According to one aspect of the invention, the light source 124 is a wavelength selective light source or a plurality of wavelength selective light sources, which may be used with any camera type. The wavelength selective light source(s) may be multi-wavelength and tunable. The wavelength selective light source may thus provide a spectrally narrow light source. The emission spectrum of the wavelength selective light source may be tuned to a spectral region of interest. The spectral selection may be performed at a source level and therefore a broadband camera can be used directly for imaging.

Figure 7:
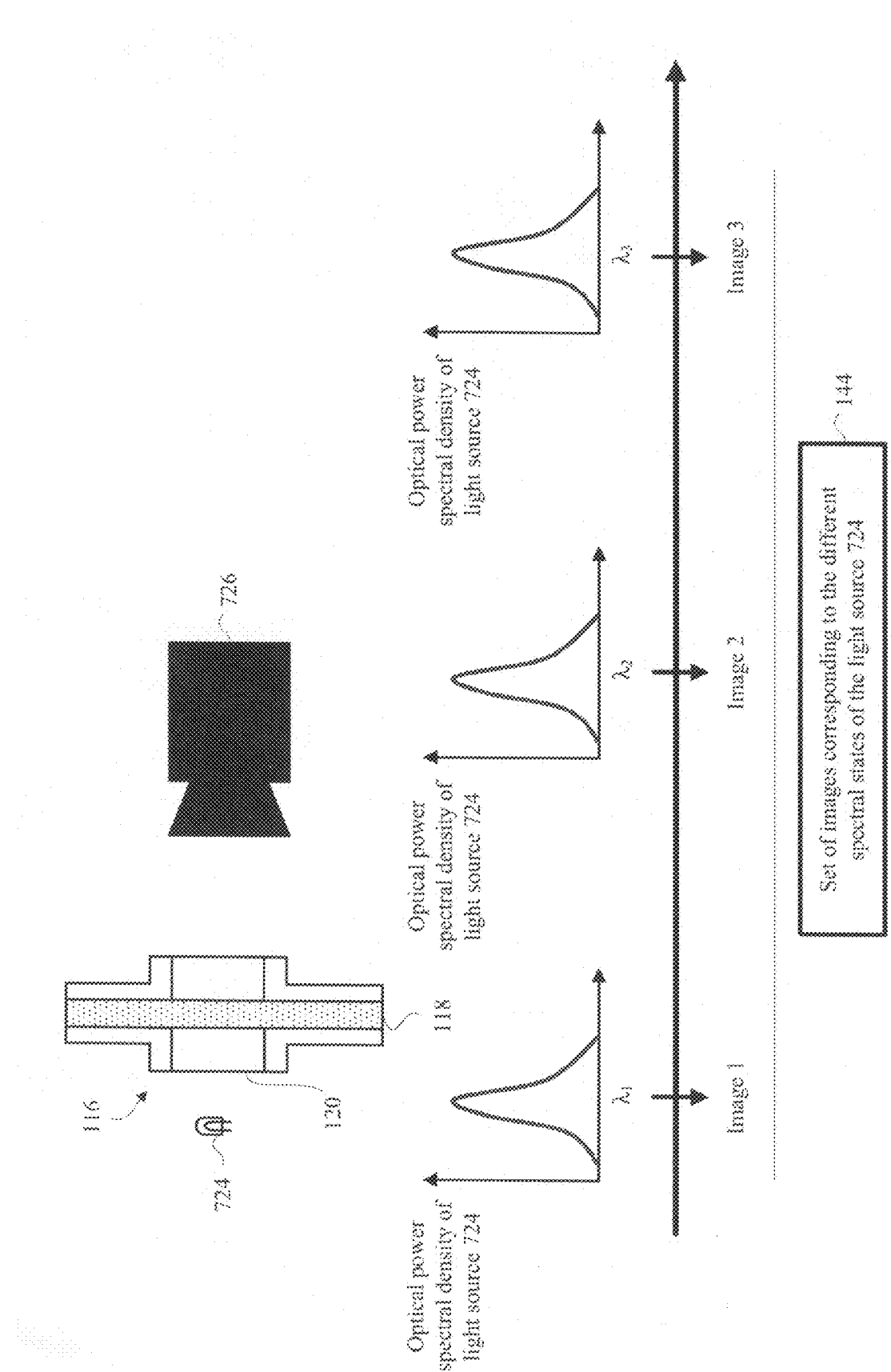
FIG. 7 illustrates a schematic for downhole fluid spectral imaging with a tunable/multi-wavelength light source according to one aspect of the present invention.

FIG. 7 illustrates the imaging process associated with a multi-wavelength light source 724, along with a possible optical layout. The light source emission spectrum can be changed and sequentially switched from one state to another as shown. FIG. 7 illustrates light source emission changed sequentially from $\lambda_1$, to $\lambda_2$, and then to $\lambda_3$. Image acquisition may be synchronized with light spectrum switch sequence in order to produce an image for each emission state as represented by box 144.

Figure 8:
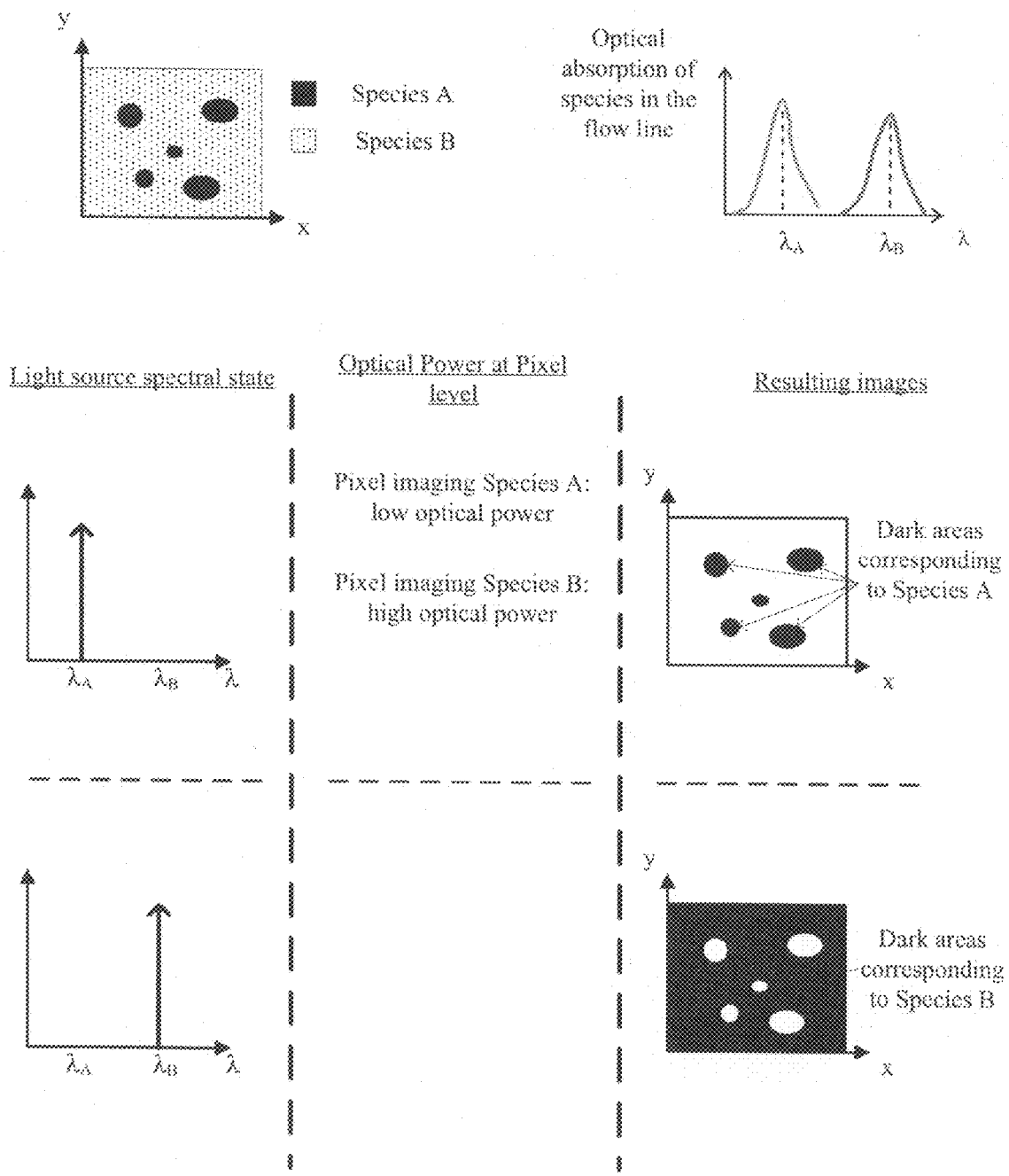
FIG. 8 illustrates downhole discrimination between two species having different optical absorption by spectral imaging with a tunable/multi-wavelength light source according to one aspect of the present invention.

FIG. 8 illustrates an example of applying the process described above to a sample in order to differentiate two species of a sample having different optical absorption properties. For example, according to FIG. 8, Species A may be a hydrocarbon and Species B may be water. In the example, the sample may be imaged in the NIR range. Several light source types may be used to implement the process, including, but not limited to: (a) a light source emitting at single or multiple fixed wavelengths, (b) a tunable light source, and (c) a broadband light source with a spectral camera. Each of the identified sources is described in more detail below.

Within the category of light sources emitting single or multiple fixed wavelengths, one of various options may be used. For example, implementing a light source for the emission of fixed wavelengths may comprise using a broadband light source such as an incandescent lamp with a combination of optical filters, which may include polarizers to enable distinction between wax and asphaltenes. The filters may be mounted on a turning wheel according to some embodiments in order to change the spectral region of interest. Another approach may be the use of an intrinsically spectrally narrow light source such as a laser. Semiconductor laser diodes (LDs), for example, may be used according to some embodiments, as most of the spectral range from visible to NIR can be covered by commercially available LDs. Light emitting diodes (LEDs) may also be used as a fixed wavelength light source. As with LDs, LEDs covering most or all of the spectral range from visible to NIR are commercially available.

Several options for producing a tunable light source are available as well. For example, a broadband light source may be used with a tunable spectroscopic section. The spectroscopic section filtrates the emitted light with the spectral range of interest. Another option may be an interferential filter, changing the orientation of the filter in front of the light source. Further, a directly tunable spectrally narrow light source may be used. For example, the emission wavelength of an LD can be tuned by changing the temperature of the laser. Temperature of the laser may be controlled by mounting the laser on a thermoelectric (TEC) module. Similar solutions may also be implemented with an LED.

A broadband light source may also be used with a spectral camera to achieve the principles of the present invention. Using a broadband light source without additional components requires spectral analysis at a camera level. A spectral camera used according to principles of the present invention may comprise a broadband sensor in combination with a spectrometer section.

Figure 9:
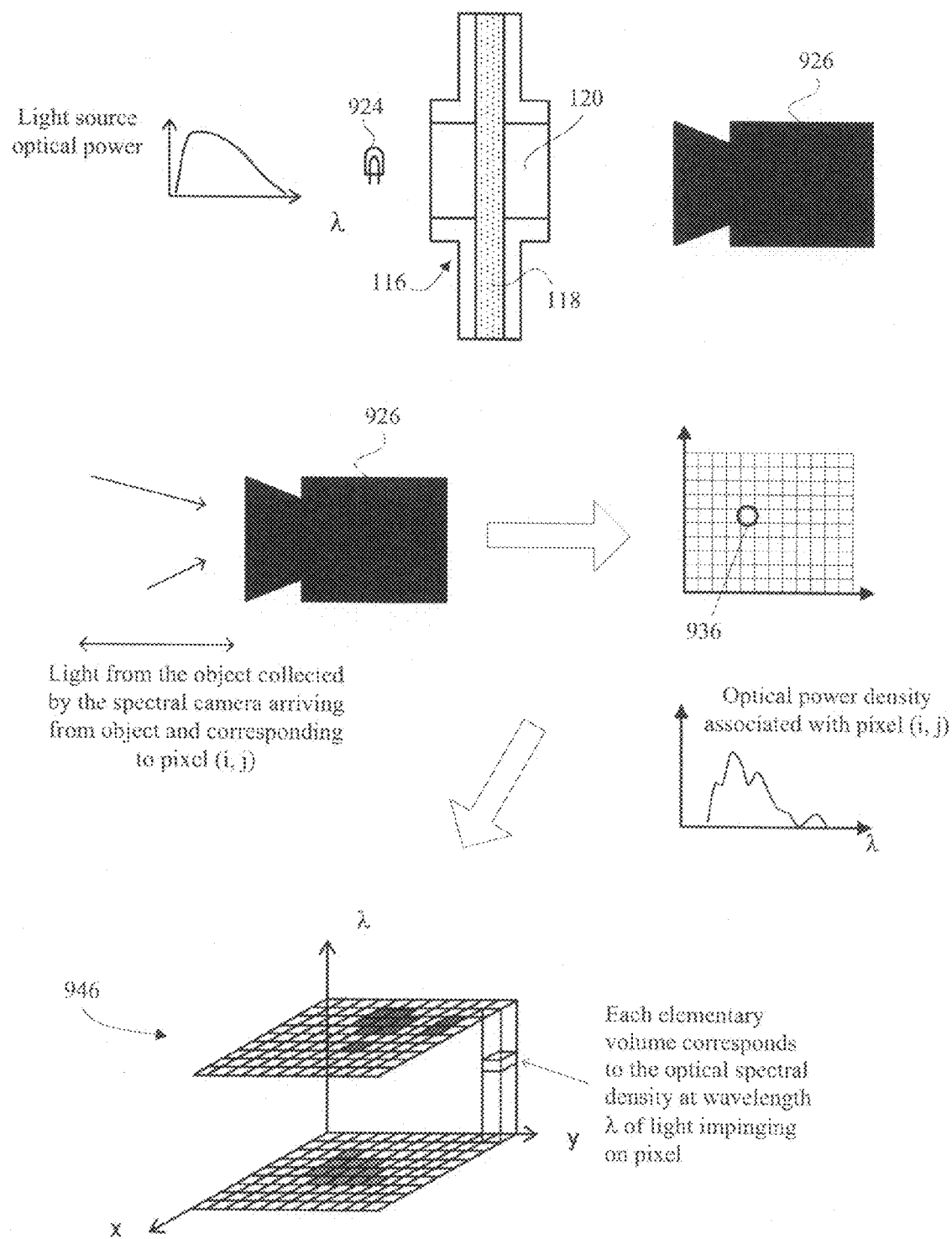
FIG. 9 illustrates downhole spectral imaging with a spectral camera according to one aspect of the present invention.

Like a broadband camera, a spectral camera 926 with a broadband light source 924 shown in FIG. 9 produces an image made of elementary pixels 936. Each pixel 936 is associated with an elementary area of the object to be imaged. The camera optics collect light from each elementary area, process the light, and provide a spectral analysis for each pixel 936 as illustrated in FIG. 9. The image can not be represented in a 2D plan in B/W or color without losing information. One possible representation is a spectral cube 946 shown in FIG. 9. The spectral cube 946 provides a representation in three dimensional (3D) space (x, y, $\lambda$) of the optical spectrum associated with each pixel. Therefore, spectral information may be retained as part of a video image for fluid characterization according to principles of the present invention. The prior art, on the other hand, is limited to pixel video imaging. The principles of the present invention may provide video images including pixel information and additional information (e.g. spectral or other information).

Figure 10:
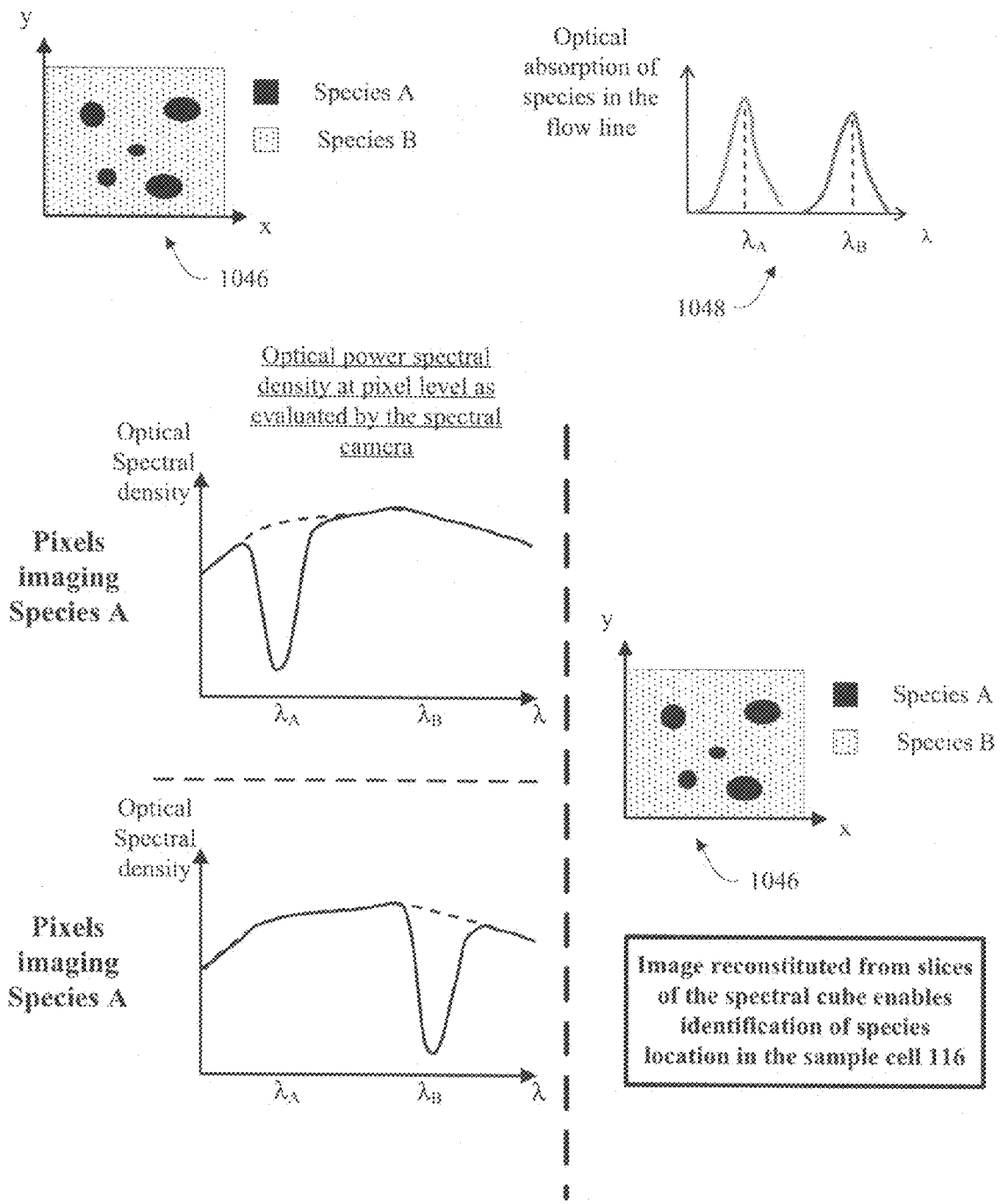
FIG. 10 illustrates downhole discrimination between two species having different optical absorption by spectral imaging according to one aspect of the present invention.

FIG. 10 illustrates one example of imaging according to the principles described above with reference to FIG. 9. Again, for purposes of discussion, Species A may be hydrocarbon and Species B may be water, which are imaged in the NIR range. As shown in FIG. 10, the imaging process may include a display of the separate locations and the optical absorption of the various species contained in a sample. Image 1046 illustrates the locations of Species A and B, and chart 1048 illustrates the optical absorption of each species. Optical power spectral density at pixel level may be evaluated by the spectral camera for multiple species, such as Species A and B as shown in FIG. 10. Thereafter, the image 1046 is reconstituted from slices of the spectral cube 946 (FIG. 9), which makes it possible to identify the species location in the sample cell 116 (FIG. 9)

Spectral imagers for 2D application can be separated into one of three general categories: liquid crystal tunable filters (LCTF), acousto-optic tunable filters (AOTF), and interferometer imagers.

LCTFs comprise a sandwich of polarizer material between birefringent plates of various thicknesses. A transmission curve of the LCTF assembly depends on the thickness of the birefringent layers and on their respective birefringence. One of the birefringent layers is preferably a cell filled with liquid crystal. By applying a voltage to the layer filled with liquid crystal, the birefringence may be changed to tune the transmission curve of the filter.

AOTFs are a well-known technology for the implementation of spectral imaging. An optic is used to collimate the light from the light source. The collimated beam then passes through the AOTF. The AOTF may be used as an optical filter.

The use of an interferometer imager is also possible to perform the spectral analysis of the image. Those of skill in the art having the benefit of this disclosure will understand the use of the interferometer.

The various examples described above for spectral imaging may not provide instantaneous measurement at some wavelengths, however, the overall result has proven to be very useful.

Alternatively, 1D spectral imaging associated parallel read-out of the image at several wavelengths may also be done. One method for simultaneous and parallel readout of image and spectroscopic information may be the use of a beam splitter associated with several image sensors. For example, a light beam from the object or fluid to be imaged is split into several beams. Each beam is refocused on a separate image sensor. Each image sensor is associated with an optical filter that is tuned to the spectral range of interest. It should be noted that optical filters can also be applied directly to the image sensor at a pixel level, which is common with digital cameras for Red-Green-Blue (RGB) encoding and provides parallel readout of wavelength.

Figure 11:
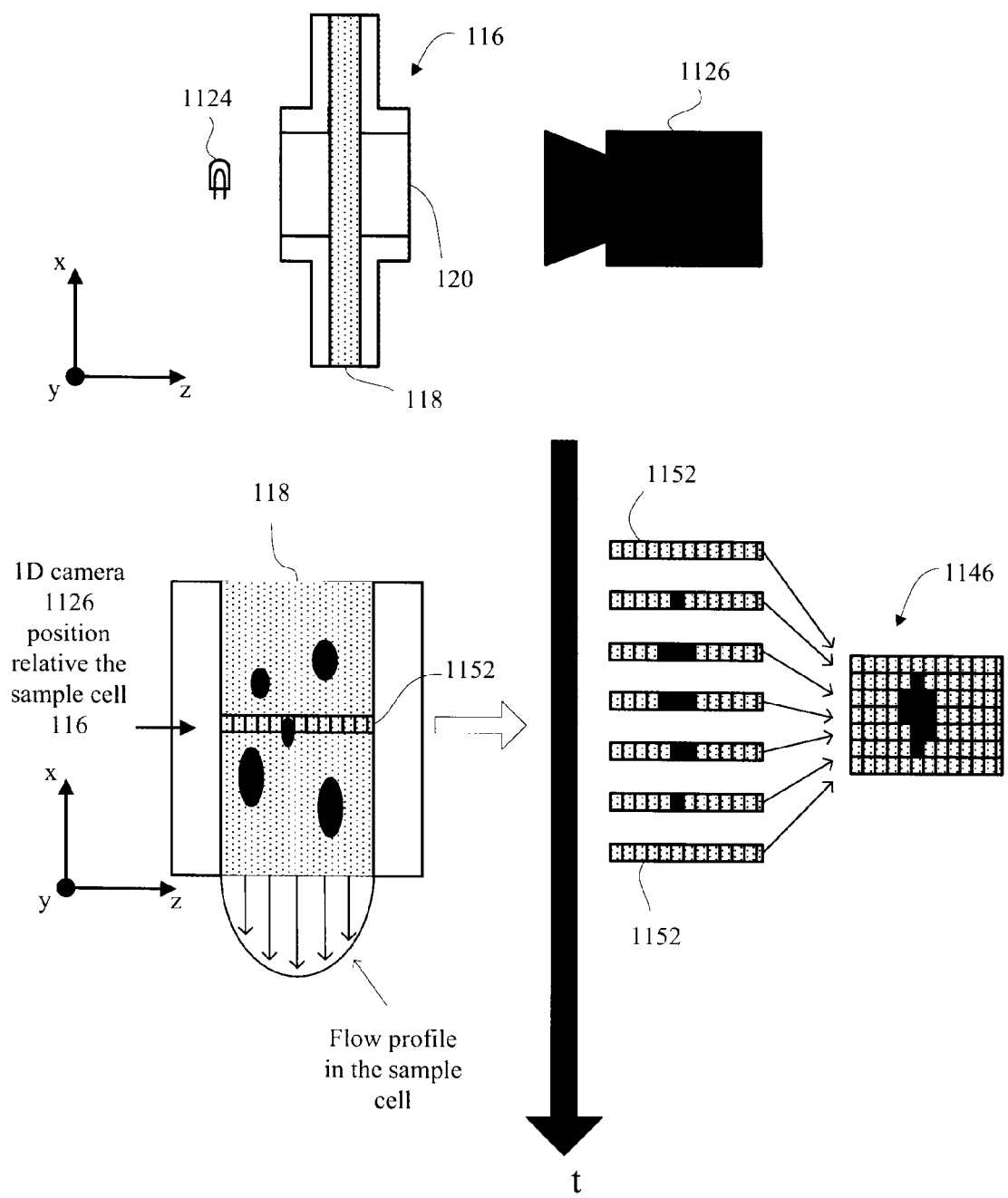
FIG. 11 illustrates a schematic for downhole imaging in a flowing fluid condition using a one dimensional image sensor according to one aspect of the present invention.

The use of a 1D sensor may be of special interest in conjunction with a flowing sample in the flow line 118. As shown in FIG. 11, if the sample fluid is moving with respect to a sensor (e.g. camera 1126), it is possible to reconstitute a partial image 1146 of the fluid flowing through the flow line 118. The 1D camera 1126 is located in a fixed position relative to the sample cell 116. Therefore lines of pixels 1152 are imaged over time, then combined or reconstituted to form the partial image 1146. Even if the partial image 1146 does not provide an exact image of the sample flow through the flow line 118, it provides useful information. In particular, in the case of a fast moving sample fluid, the read-out data rate of a 2D imaging sensor may be too slow to provide continuous imaging of the sample. However, by using the 1D camera 1126 or other 1D sensor, a much faster read-out rate can be achieved, facilitating continuous imaging of the sample fluid through the flow line 118. Another advantage of the 1D camera 1126 is a reduction in the volume of data transmitted uphole via a telemetry system.

According to some aspects of the invention, the downhole fluid samples themselves may generate light. For example, certain artificial light sources can lead to sample fluorescence. A spectral camera such as the one referenced above may be used to perform a spectral, as well as spatial analysis of fluorescence in order to increase phase behavior understanding. Oil is known to exhibit fluorescence when illuminated by blue light. Water, on the other hand, does not exhibit fluorescence when illuminated by blue light. Therefore, according to some aspects of the present invention, spectral imaging of sample fluorescence may be used to identify and differentiate water and oil downhole.

Figure 12:
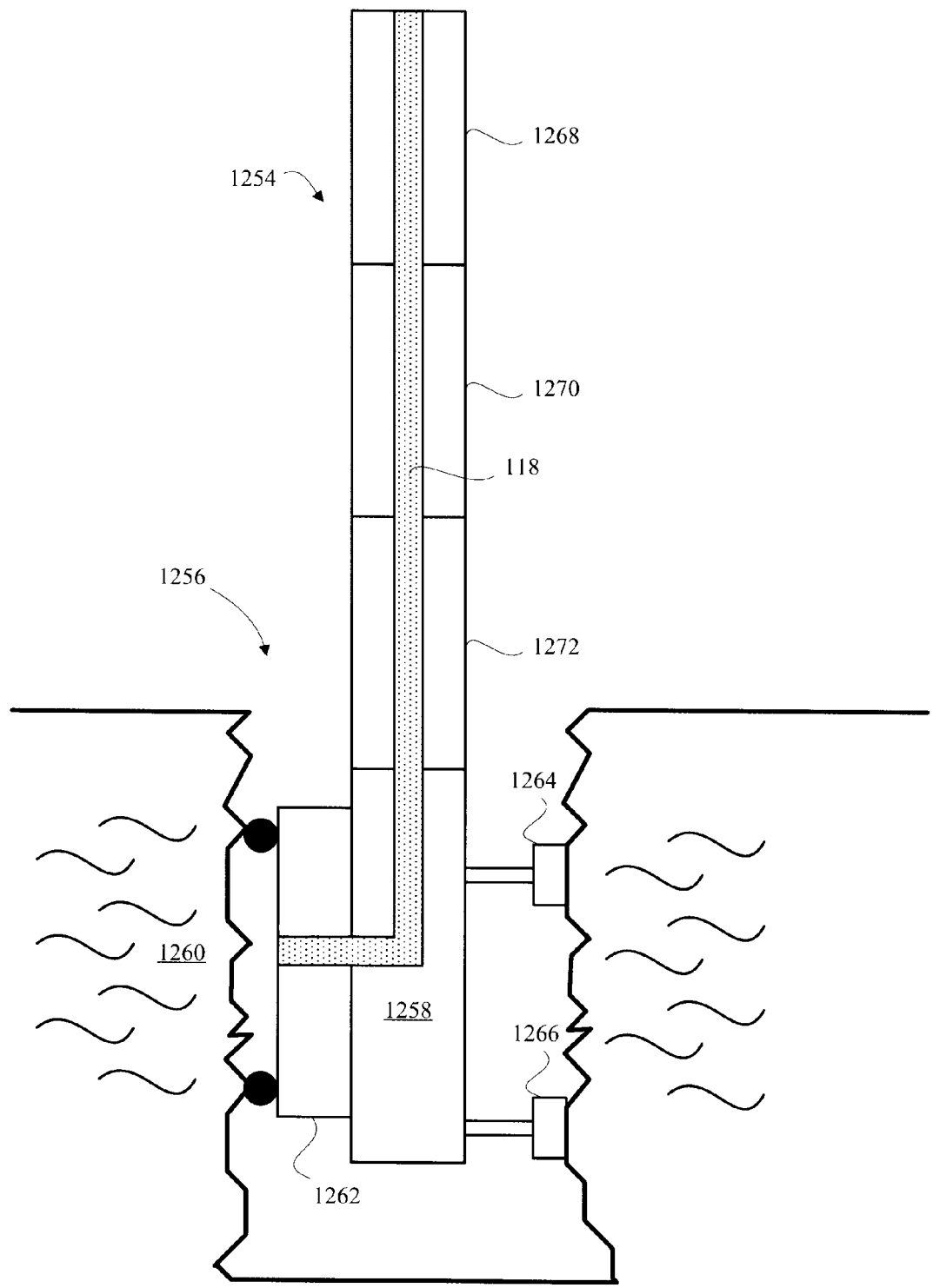
FIG. 12 illustrates an application of downhole image fluid characterization to a downhole environment according to one aspect of the present invention.

The methods and imaging systems described herein and others may be implemented downhole via a wireline device such as a downhole sampling tool 1254 shown in FIG. 12. The downhole sampling tool 1254 is shown deployed in a borehole 1256 and includes a sampling probe module 1258. The sampling probe module 1258 is adjacent to and in contact with a formation 1260 containing a fluid of interest. The sampling probe module 1258 includes a pump-out module 1262 comprising first and second support legs 1264, 1266 and an opening for fluid communication with the flow line 118. A pump disposed in a pump module 1268 facilitates extraction of fluid from the formation into the flow line 118.

Figure 13A:
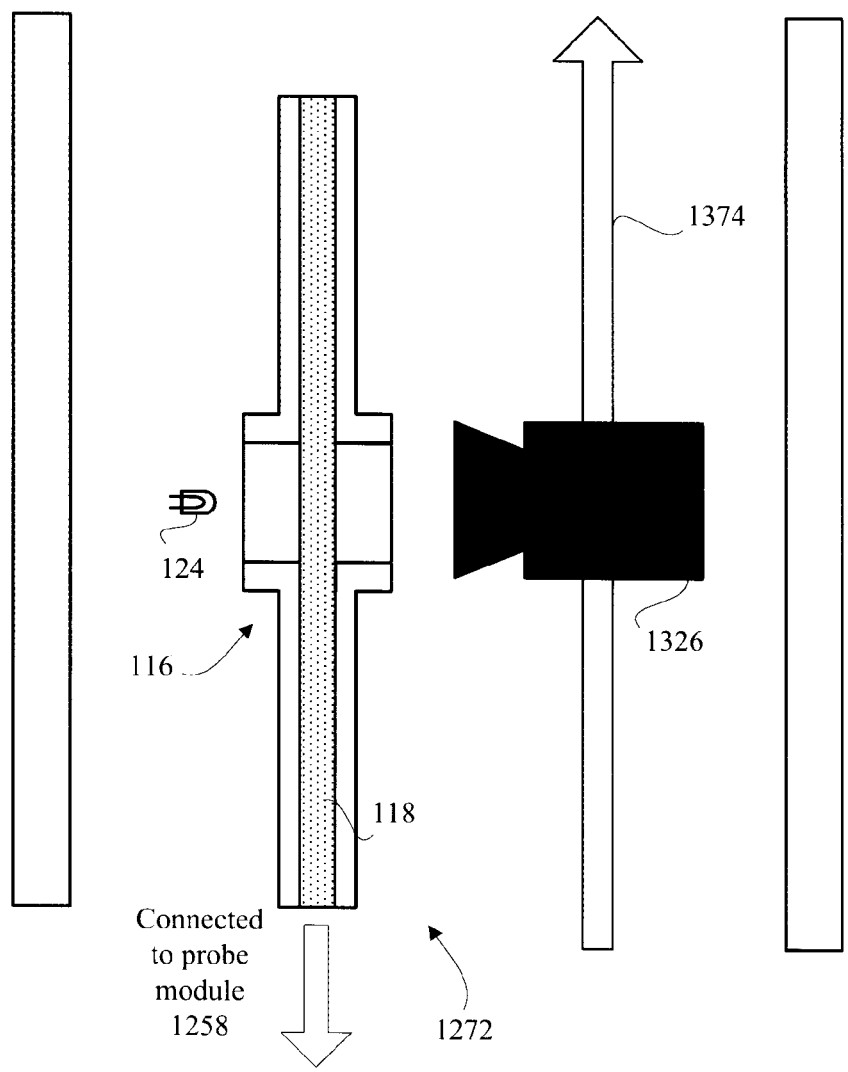
FIG. 13a illustrates a schematic for a downhole video imaging module with sample quality assurance for fluid characteristic measurement according to one aspect of the present invention.
Figure 13B:
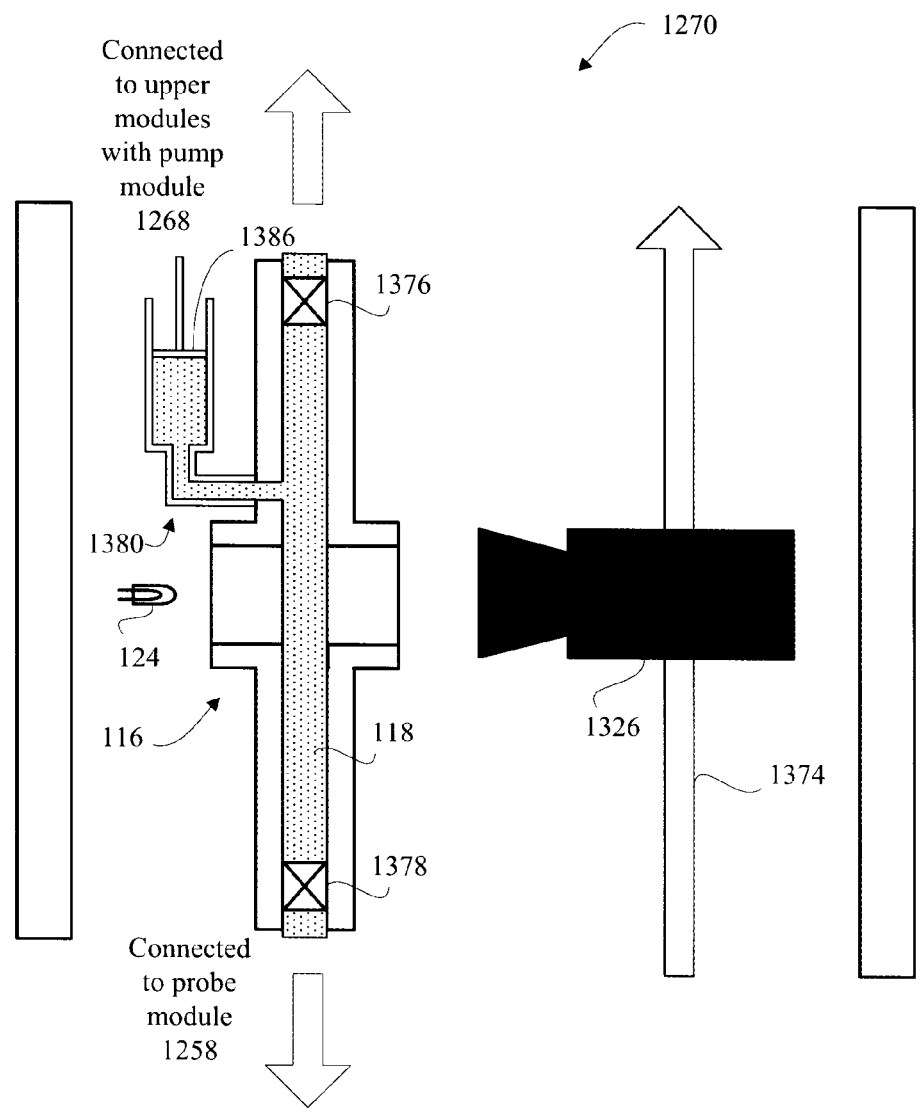
FIG. 13b is a schematic diagram of a downhole PVC module and associated video camera for fluid characterization measurement according to one aspect of the present invention.

The flow line 118 may provide a static or continuous flow of sample fluid to a downhole lab module 1270, which may include a pressure-volume control unit and one of the imaging systems described above. In addition, the downhole sampling tool 1254 may include a sample quality assurance video module 1272. Details of one embodiment of the sample quality assurance video module 1272 are shown in FIG. 13a. Details of one embodiment of the downhole lab module 1270 are shown in FIG. 13b.

Referring to FIG. 13a, a camera 1326 (which may comprise any of the cameras described above) is preferably disposed directly adjacent to the flow line 118. The camera 1326 is preferably set to a high shutter speed that can be synchronized with fluid flow rate through the flow line 118. The camera 1326 is operatively connected to a telemetry bus 1374 and may be used to monitor the sample fluid for contamination and single-phase flow. As mentioned above, imaging enables the detection of liquid-liquid split, gas bubbles, solid particles, and can discriminate between water and hydrocarbon.

Monitoring for single-phase flow may be of particular importance. As formation fluid is pumped through the flow line 118, it tends to depressurize to some degree (depending on the magnitude of the pressure drawdown). Depressurization may lead to asphaltene precipitation, apparition of gas bubbles, or other multi-phase phenomena. In order to retrieve (and/or characterize downhole by video imaging) a sample representative of the formation fluid, it is important to avoid all phase changes. Accordingly, by monitoring phase behavior of the fluid during sampling via video imaging, it is possible to adjust pumping conditions to prevent phase changes from taking place, change other operating parameters, or refrain from retrieving a sample to surface.

The downhole lab module 1270 may comprise any of the video imaging configurations (connected to the telemetry bus 1374) shown and described above or others. The present invention contemplates any downhole video monitoring of formation fluid characteristics. In addition, the downhole lab module 1270 may include an arrangement as shown in FIG. 13b. The downhole lab module 1270 may be dedicated to downhole fluid characterization. The module 1270 may include first and second seals such as seal valves 1376, 1378 to isolate a fluid sample. The light source 124, camera 1326, and sample cell 116 are thus disposed between the first and second seal valves 1376, 1378. Moreover, the downhole lab module 1270 may include a pressure-volume control unit 1380 controlling the pressure and volume of the isolated sample fluid. The PVC unit 1380 generates pressure changes. After the sample is trapped between the first and second seal valves 1376, 1378, a piston 1386 is then operated in order to reduce the pressure and generate fluid phase change. The camera images are recorded as a function of piston position and fluid pressure. The camera 1326 is then used to detect phase changes. The camera 1326 makes it possible to identify phase changes. The camera 1326 may be used to identify bubble point, asphaltene, and wax precipitation point. Therefore, the camera 1326 may be used as described herein to monitor sample phase behavior and characterize the sample fluid downhole. The camera may enable viewing of details down to a light diffraction limit. Therefore, the camera may be selected to resolve targeted details in the range of a few micrometers. The information related to the sample fluid may be transmitted uphole via the telemetry bus 1374.

Figure 14:
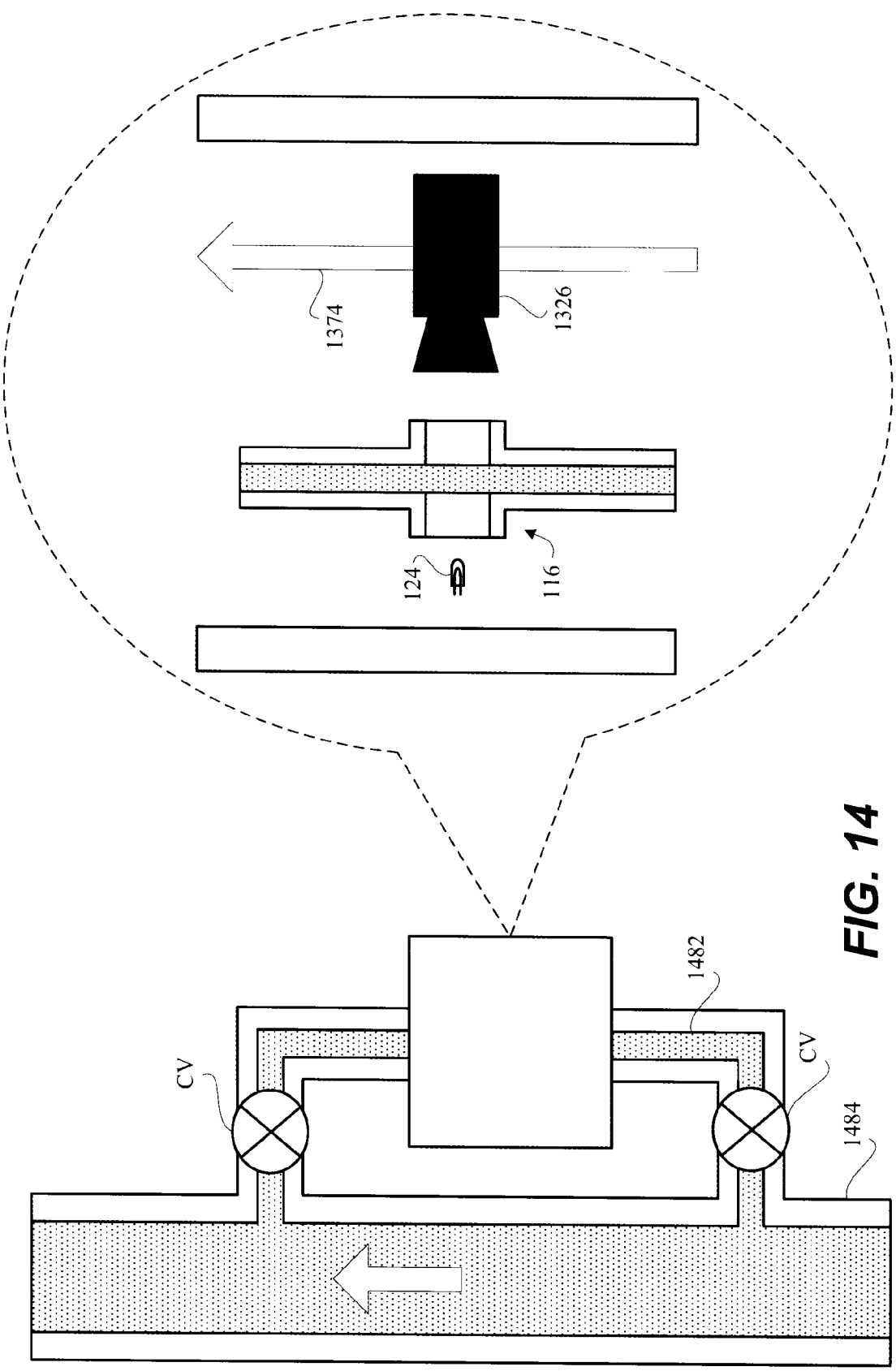
FIG. 14 is a schematic diagram illustrating a bypass for sub-sample visualization during fluid flow in a sub-sea flow line and implementation of a permanent production camera system according to one aspect of the present invention.

In addition to temporary monitoring such as by the wireline configurations discussed above, the principles of downhole video monitoring according to the present invention may be applied to facilitate fluid characterization in permanent production monitoring systems. In a permanent video monitoring assembly, a sampling apparatus may comprise a by-pass 1482 connecting a production line 1484 to the sample cell 116 as shown in FIG. 14. By-passes for fluid sampling in production conditions have been shown to produce satisfactory results. Of course any of the video systems and methods described above and others may be used in a permanent installation, thus the assembly is not limited to the embodiment shown in FIG. 14.

The implementation of the camera 1326 downhole as part of a permanent assembly facilitates characterization of the phase behavior under production conditions. In particular, the permanent installation of the embodiment of FIG. 14 facilitates identification of solid phases that could result from asphaltene or wax precipitation. The management of precipitation phenomenon is of particular importance during oil production. Precipitates can agglomerate and stick to production casing, leading to a flow restriction. In some cases precipitates can plug production tubing.

Solid precipitation has led to the development of injected chemical treatments to reduce precipitation. However, prior to the present invention, the efficiency of treatment products has been difficult to assess in downhole conditions due to the lack of in situ validation.

Another application according to the present invention may include installation of downhole imaging systems at different locations along the borehole and/or production tubing. By monitoring phase behavior at different locations along a flow path, it is possible to quantify the effect of injected chemical (if any) and, in turn, optimize or improve the location of chemical treatment injection points. Using imaging analysis of the captured photomicrographs at different locations (which correspond to different pressures, temperatures, and/or compositions) downstream from the chemical injection depth, the operator may assess the efficiency of and optimize the dosage of a chemical treatment in real time. Information such as the size of solid particles, volumetric concentration, and distribution are key parameters for the assessment of chemical treatment efficiency and can be discerned by video analysis according to the principles described herein. Oil/water ratios may also be monitored via wireline or permanent installations. The use of a dual camera system located some distance apart in the wellbore opens the way to the determination of fluid velocity through cross-correlation techniques, possibly in combination with automated image analysis techniques, and may also facilitate determination of the individual velocity and volume fraction for each phase.

Figure 15:
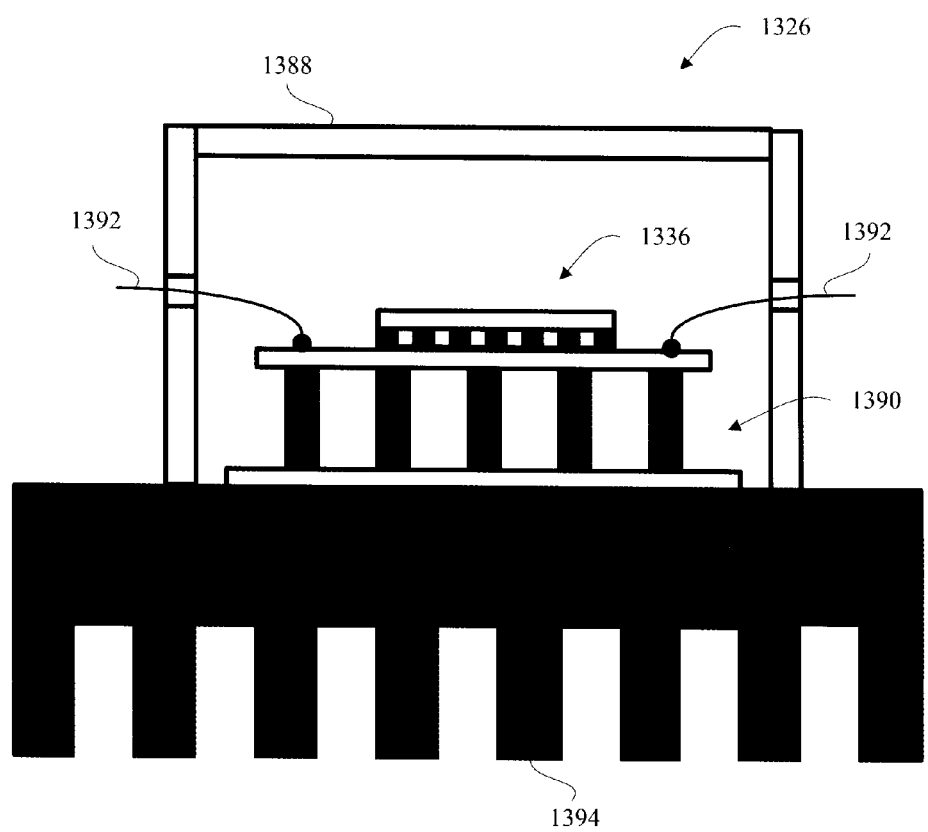
FIG. 15 illustrates an active camera cooling system that may be used according to embodiments of the present invention.

The cameras described above may be actively cooled to facilitate use downhole in high temperature environments. For example, each of the cameras described above may include the active cooling arrangement shown in FIG. 15, however, any active cooling arrangement may be used. As shown in FIG. 15, the camera 1326 may include a window 1388 housing the image sensor 1336. The image sensor 1336 is cooled by a thermoelectric cooler 1390 or other cooling mechanism, such as a sterling cooler. Wiring 1392 provides an electrical connection between the image sensor and outside circuitry. It will be understood by those of skill in the art having the benefit of this disclosure that the cold face of any active cooler may include any electronic device that may be necessary to drive the image sensor. For example, a more compact device may be made by using a multi-chip module (MCM) technique for packaging with a Peltier face used as a ceramic substrate of the MCM. Accordingly, the most sensitive electronics may be located in the cooled environment. The thermoelectric cooler 1390 may be thermally connected to a thermal dissipater, such as the finned thermal dissipater 1394 shown in FIG. 15. The housing may be vacuum sealed to improve cooling efficiency. Although specific examples are described above, any active cooling system may be used according to the principles of the present invention to cool the camera 1326 or other electronics.

The preceding description has been presented only to illustrate and describe the invention. It is not intended to be exhaustive or to limit the invention to any precise form disclosed. Many modifications and variations are possible in light of the above teaching.

The preferred embodiments were chosen and described in order to best explain the principles of the invention and its practical application. The preceding description is intended to enable others skilled in the art to best utilize the invention in various embodiments and with various modifications as are suited to the particular use contemplated. It is intended that the scope of the invention be defined by the following claims.

What is claimed is:

1. A method of monitoring subterranean formation fluids, comprising:
    pumping a formation fluid sample into a sample cell downhole;
    isolating the fluid sample;
    controlling pressure and volume of the isolated fluid sample by using a piston;
    characterizing a formation fluid sample downhole with a video imaging system;
    wherein the video imaging system performs pixel imaging and additional imaging,
    wherein the additional imaging comprises spectral imaging,
    wherein the spectral imaging is configured to provide a spectral analysis for each pixel, and
    wherein the characterizing the formation fluid sample comprises characterizing a fixed sample in the video imaging system with recording as a function of a position of the piston.

2. A method of monitoring subterranean formation fluids according to claim 1, further comprising using a spectrally broadband light source in combination with a spectral imaging video camera downhole.

3. A method of monitoring subterranean formation fluids according to claim 1, further comprising using a tunable or multi-wavelength light source in combination with any camera.

4. A method of monitoring subterranean formation fluids according to claim 1, wherein the characterization comprises two-dimensional imaging and analysis.

5. A method of monitoring subterranean formation fluids according to claim 1, wherein the characterizing further comprises flowing the fluid sample through the video imaging system.

6. A method of monitoring subterranean formation fluids according to claim 5, wherein the characterizing comprises one-dimensional, in-line imaging and analysis.

7. A method of monitoring subterranean formation fluids according to claim 6, wherein the one-dimensional imaging comprises:
    successively acquiring one-dimensional flow line images;
    reconstituting two or more of the one-dimensional flow line images into a two-dimensional image.

8. A method of monitoring subterranean formation fluids according to claim 1, wherein the characterizing comprises generating three-dimensional flow line images with the video imaging system.

9. A method of monitoring subterranean formation fluids according to claim 8, wherein the three-dimensional flow line images are generated using downhole confocal microscopy.

10. A method of monitoring subterranean formation fluids according to claim 1, further comprising actively cooling the video imaging system downhole.

11. A method of monitoring subterranean formation fluids according to claim 1, further comprising relating video imaging data from the video imaging system uphole via a telemetry bus or temporarily retrievable memory chips.

12. A method of monitoring subterranean formation fluids according to claim 1 wherein the additional imaging comprises implementing a high pressure microscope downhole and a cross polarizer in front of the high pressure microscope for wax detection.

13. A method of monitoring subterranean formation fluids according to claim 1, wherein the video imaging system comprises a back-scattered imaging configuration.

14. A method of monitoring subterranean formation fluids according to claim 1, wherein the characterizing the formation fluid sample further comprises detecting phase changes.

15. A method of monitoring subterranean formation fluids, comprising:
- pumping a formation fluid sample into a sample cell downhole;
- isolating the fluid sample;
- controlling pressure and volume of the isolated fluid sample by using a piston;
- characterizing a formation fluid sample downhole with a video imaging system;
- wherein the video imaging system performs pixel imaging and additional imaging,
- wherein the additional imaging comprises spectral imaging,
- wherein the spectral imaging is configured to provide a spectral analysis for each pixel, and
- wherein the characterizing the formation fluid sample comprises characterizing a fixed sample in the video imaging system with measuring and controlling pressure of the fixed sample and recording as a function of a position of the piston.

* * * * *